(12) United States Patent
Kaufmann et al.

(10) Patent No.: US 7,414,703 B2
(45) Date of Patent: Aug. 19, 2008

(54) SCATTERED LIGHT RANGE OF VIEW MEASUREMENT APPARATUS

(75) Inventors: Juergen Kaufmann, Denzlingen (DE); Ingo Schiffler, Freiburg (DE); Klaus Smetana, Emmendingen (DE)

(73) Assignee: Sick Maihak GmbH, Waldkirch (DE)

( * ) Notice: Subject to any disclaimer, the term of this patent is extended or adjusted under 35 U.S.C. 154(b) by 0 days.

(21) Appl. No.: 11/637,627

(22) Filed: Dec. 11, 2006

(65) Prior Publication Data

US 2007/0146705 A1    Jun. 28, 2007

(30) Foreign Application Priority Data

Dec. 13, 2005    (EP) .................................. 05027138

(51) Int. Cl.
*G01C 3/08* (2006.01)
(52) U.S. Cl. ..................................... 356/4.01
(58) Field of Classification Search .................. 356/4.01
See application file for complete search history.

(56) References Cited

U.S. PATENT DOCUMENTS 4,346,293 A * 8/1982 Fetzer ..................... 250/222.1

6,266,136 B1 * 7/2001 Ramer et al. ........... 356/139.03
2004/0051860 A1 * 3/2004 Honda et al. ............... 356/4.01

FOREIGN PATENT DOCUMENTS

| EP | 0036370 A1 | 9/1981 |
|---|---|---|
| EP | 0664445 A2 | 7/1995 |

* cited by examiner

*Primary Examiner*—Thomas H. Tarcza
*Assistant Examiner*—Luke D Ratcliffe
(74) *Attorney, Agent, or Firm*—Townsend and Townsend and Crew, LLP

(57) ABSTRACT

A method and apparatus for determining a range of sight which are capable of monitoring and correcting the operability of the instrument. A light emitter directs an emitted light beam to a measurement zone and a light receiver receives a received light beam from the measurement zone. The emitted light beam and the received light beam cross each other in the measurement zone. A deflector deflects at least a portion of the emitted light beam downstream of the measurement zone along a light transmitting path and directs the portion of the emitted light beam into the received light beam at a side of the measurement zone opposite from the light receiver. An optical shutter intermittently closes the light transmitting path in a temporally controlled manner.

15 Claims, 2 Drawing Sheets

SCATTERED LIGHT RANGE OF VIEW MEASUREMENT APPARATUS

RELATED APPLICATIONS

This application claims the priority of European patent application No. 05 027 138.6 filed Dec. 13, 2005, the disclosure of which is incorporated herein by reference.

BACKGROUND OF THE INVENTION

The invention concerns a scattered light range of sight measurement instrument which measures the amount of light scattered by a light beam as it traverses a gas sample from which the density of particulates in the gas sample can be established. With this information, the sight range or viewable distance through the sample can be determined.

Stray or scattered light measuring instruments are used for determining the presence of particles (aerosols, dust, etc.) in venting conduits as well as in the atmosphere as a whole. For example, the carbon particle emissions from a chimney can be determined in this way. Scattered light measuring instruments are further used in street traffic, ocean shipping and air transport, and they are used, when appropriate, to generate a warning signal when a predetermined range (or distance) of sight becomes too low, e.g. exceeds a lower threshold value.

Such instruments employ either the transmission principle or the light scattering principle.

Range of sight measuring instruments employing the transmission principle, also sometimes referred to as transmissometers, direct a predefined amount of light into one end of a measuring distance. The emitted light is received by a light receiver located at the other end of the measurement distance where the incoming light volume is measured. If there are no particles along the measuring distance, the receiver receives 100% of the emitted light. The mathematical relationship between the length of the measuring distance and the transmission value measured at the receiver can be used to determine the distance or range of sight through the air or gas sample being measured.

Instruments which, for example, include an optical reflector and direct the light beam several times over the measurement distance, and only then determine the amount of received light, are also transmissometers.

Sight range measuring instruments which measure light scattered by particulates in the sample being measured also employ a light emitter and a light receiver. The emitter and receiver are arranged so that an emitted light beam from the light emitter and a received light beam striking the light receiver cross each other to prevent light from the emitter from directly reaching the light receiver.

When the light emitter is on one side (or upstream) of the measurement zone and the light receiver is on the other side or downstream of the zone, and particulates in the gas sample are to be detected, the so-called forward-scattering principle is employed.

On the other hand, if the light emitter and receiver are both on the same side of the measurement zone, the so-called back-scatter principle is employed.

Since the two light beams cross each other, no light from the emitter can directly reach the light receiver. The receiver can only receive a portion of the emitted light beam when the emitted light strikes a particle inside the measurement zone, because the particle will scatter the light in multiple directions. Accordingly, as the density of the particles in the measurement zone increases, the light receiver receives proportionally more light, which indicates a reduced viewing range or distance through the sample.

Although scattering light instruments have many advantages as compared to transmissions instruments, a significant disadvantage of them is that with good sight only a very small amount of light is received by the light receiver. For example, the testing of the functionality of the individual components of the instrument and assembly groups requires additional steps. If the light emitter were to cease to operate due to a defect, there would be no light that is directed or scattered towards the light receiver even when the particle concentration in the measurement zone is high. Instead, the instrument would interpret such a reading as indicating an extremely good or long range of sight. According to published German patent application No. DE 19 05 016, such errors are precluded by closing the light path from the light scattering particles to the light receiver at regular, short intervals, during which no scattered light from the particles can reach the light receiver. During this time interval, a predetermined amount of test light is directed from the light emitter directly to the light receiver. In this manner, several components of the light scattering instrument can be monitored with regard to their functionality. However, a disadvantage of this is that this manner of checking for defects fails to recognize a fairly large number of possible defects. For example, it cannot be determined when the emitted light beam and/or the received light beam are completely interrupted by a large surface obstacle which would prevent light from reaching the light receiver. As a consequence, the scattered light instrument interprets this occurrence as indicating a large viewing distance. Further, any progressively increasing contamination of optical boundary surfaces cannot be recognized because the boundary surfaces are also not in the optical path of the test light directed to the light receiver.

Further suggestions for correcting typical problems encountered with such scattered light instruments come from German published patent application No. DE 44 01 755 A1. It proposes to integrate a transmissions arrangement in a forward-scattering instrument and by providing at least one additional light receiver, or an additional light receiver and an additional light emitter. This combined and switchable scattered light and transmitted light measurement is said to enable the correct detection of obstacles within the optical measuring distance, or to compensate for deposits on the optical boundary surfaces. The arrangement of DE 44 01 755 A1 however has the disadvantage that the use of an additional light receiver involves additional costs. Moreover, with such a transmissions measurement, effectively only half the length of the scattered light measurement distance is being tested. For this reason, the German publication points out that the additional light receiver should also have an additional light emitter. Aside from the resulting higher costs, a major disadvantage of such an arrangement is that the optoelectronic components frequently react differently to changed conditions. It can therefore not be assured that over a longer period of time this will lead to correct compensations for measuring errors due to contaminants on the optical boundary surfaces. The reason for this is that whenever small particle concentrations are present (and the line of sight is large), the useable amount of light is necessarily very small so that even relatively minor incorrect compensation values can lead to large measurement errors.

BRIEF SUMMARY OF THE INVENTION

It is therefore an object of the present invention to provide a scattered light range of sight measurement instrument, also referred to herein as a "scattered light instrument", and a method for operating it which does not have the disadvantages encountered in the past state of the art. In particular, such a scattered light range of view measurement instrument should generate an unequivocal indication of the degree of contamination at optical boundary surfaces. The present invention further seeks to prevent negative consequences such as inaccurate readings caused by changes in the components of the optoelectronic portion of the instrument. It also assures that obstructions in the optical path are correctly detected.

In accordance with the invention, the scattered light instrument directs at least a part of the emitted light beam into a light deflector after the light has traversed the measuring zone. This light then forms a transmission light path which is entrained in the light beam at the opposite side for receipt by the light receiver. The transmissions light path is periodically opened and closed with an optical shutter that may form part of the light deflector.

An advantage of the present invention is that with the periodically activated transmissions light path via the light deflector, a desired additional transmission measurement can be made. As compared to the scattered light measurement method, this generates a strong light signal for the light receiver, particularly when the range of sight is good. This then enables a functional testing of the scattered light measuring instrument. Since the transmissions light path uses the same light emitter and the same light receiver as is used during normal scattered light measurements, the instrument of the present invention has the significant advantage that possible component alterations or changes of the optoelectronic components have no effect.

A further advantage of the present invention is that the geometric spaces traversed by the light are the same and do not differ from each other. This has the advantage that obstacles that may be present in the light radiation space and the optical boundary surfaces are the same for both and can therefore be securely recognized. Such optical boundary surfaces are used in scattered light instruments to protect the instrument from dirt and contamination. Nevertheless, dirt and contaminants can deposit on these optical boundary surfaces, which can interfere with the proper functioning of the instrument. Through the activation of the transmissions light path in accordance with the present invention, even such contaminating deposits are recognized, which is not possible with conventional scattered light range measuring instruments. Since the transmissions light path cannot continuously be active, the present invention provides an optical shutter which temporally controls the opening and closing of the transmissions light path. For this, the present invention contemplates, for example, to interrupt the light path by operating the shutter with a rotatable magnet. It is also possible to operate the shutter with a stepping motor, a magnetic cylinder or other suitable drive units.

If it is not possible to place the optical shutter in the transmissions light path, it is advantageous to position the shutter immediately in front of, behind or within the light deflector to avoid adverse interferences from other reflections that can occur in the instrument.

In a particularly preferred embodiment, the light deflector is constructed of either a flexible or a rigid light conduit or conductor. Especially the use of a flexible light conductor is useful because the light transmissions path can then be easily conformed to the encountered geometric configuration of the instrument.

The use of a light conduit for the light deflector further increases its effectiveness because the amount of light which is relayed via the transmissions path in accordance with the present invention can be increased by placing connecting optics at the respective ends of the light conduit. The reason for this is that a convex lens positioned at the correct distance from the light conduit has an opening that is significantly larger than the cross-section of the light conduit. As a result, a greater amount of light can be fed into the light conduit. Similarly, a corresponding connector for decoupling the light conduit has the advantage that light emitted at the other end of the conduit can be angularly directed towards the light receiver so that it receives the major portion of the light emitted by the light conduit.

For controlling the operation of the optical shutter and therewith the activation of the transmissions light path, the present invention preferably uses a timed activation system. This makes it possible to automatically control the activations of the transmissions path, the temporal spacing between shutter openings, and the duration of the openings. In this manner, the operation of the scattered light instrument can be optically adapted to the encountered installation and requirements.

In another embodiment of the present invention, a signal processing unit accumulates over a predeterminable time interval the values measured while the optical shutter was open. Thus, even slow changes in the measured values, for example due to a gradually increasing contamination of individual optical boundary surfaces, can be recognized and adverse effects resulting therefrom can be corrected, for example by generating a corresponding warning signal or message.

DETAILED DESCRIPTION OF THE INVENTION

Figure 1:
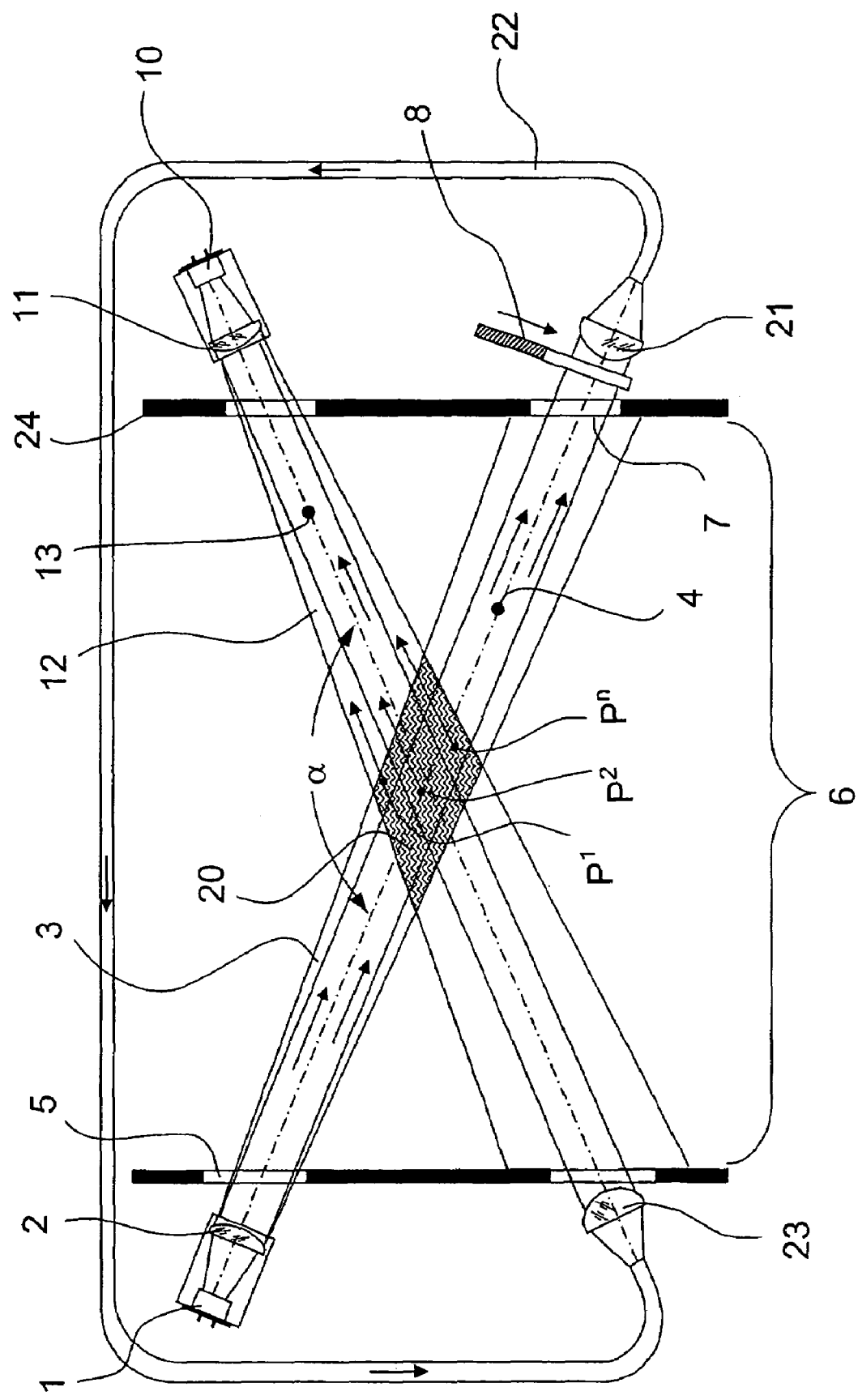
FIG. 1 schematically illustrates a range of view measuring instrument or apparatus constructed in accordance with the present invention that is based on the forward-scattering measurement principle.

Referring to FIG. 1, a light emitter 1 that cooperates with an associated emitting optics 2 directs an emitted light beam 3 along an axis 4 of an emitted light beam 3. The light beam 3 traverses an optical end plate 5 from which it enters a testing space 6. The light beam 3 continues and reaches another end plate 7 at the opposite end of testing space 6. After light beam 3 has traversed end plate 7, it reaches an optical shutter 8 which prevents the further expansion of the beam while scattered light is being measured.

A light receiver 10 which includes a receiving optics 11 is arranged behind a boundary 24 of testing space 6. Light receiver 10 together with receiving optics 11 collect all light that is received from a received light beam 12 and convert the received light quantity into a proportional electrical signal. Received light beam 12 has a received light beam axis 13 which crosses the emitted light beam axis 4 inside testing space 6 at an angle α Since the two light beam axes 4, 13 cross each other, the emitted light beam 3 and the received light beam 12 also cross and thereby establish a measurement zone 20. If the measurement zone is particle-free (no aerosol particles, dust particles, and the like), no part of the light of emitted light beam 3 can enter the received light beam 12 and no light reaches light receiver 10. However, if particles $P^1$, $P^2$ to $P^n$ are present in the measurement zone as is illustrated in FIG. 1, portions of the emitted light beam 3 are scattered by the particles in different directions. In such an event, some of the scattered light portions will reach light receiver 10. From the magnitude of the amount of light reaching light receiver 10, one can make a determination concerning the prevalence or density of the particles in the measurement zone, from which, in turn, it is possible to judge the range of sight through the gas sample.

However, if there is an obstacle in the area between end plate 5 and measurement zone 20 which interrupts the emitted light beam 3, no light reaches the measurement zone 20. As a result, even if there are large numbers of particles in the measurement zone, no light will reach light receiver 10 and the instrument will indicate that there is an optimal viewing range or distance through the gas sample.

To prevent such erroneous readings, the optical shutter 8 can be momentarily opened so that a portion of the emitted light beam 3 is diverted via connecting optics 21 to a light guide or conduit 22. Light conduit 22 directs the incoming light around testing space 6 to a further connecting optics 23 which directs the diverted light along the received light beam axis 13 to light receiver 10. This generates an optical transmissions path in the scattered light instrument that extends from light emitter 1 to light receiver 10. This transmission path includes the end plates that define the testing space boundaries as well as all possible optical beam directions inside the testing space, including in particular the scattered light measuring path.

In this manner, contaminations of the end plates can be observed and undesired obstacles within the optical paths can be recognized.

Figure 2:
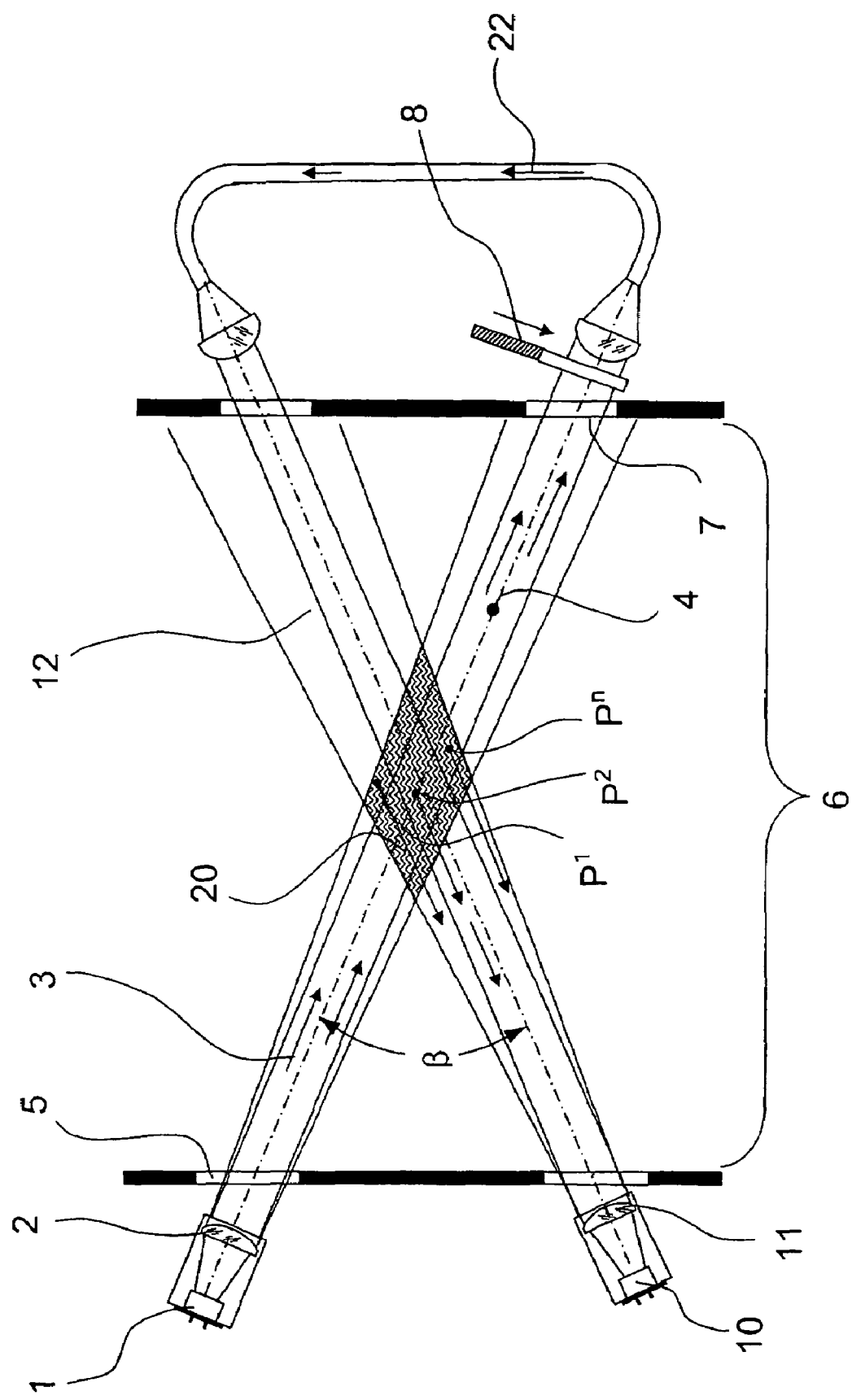
FIG. 2 is a schematic view of a range of view measuring apparatus constructed in accordance with the present invention that employs the back-scattering principle.

FIG. 2 shows a scattered light range of view measurement instrument which employs the back-scattering principle for detecting particles that might be present. This differs from what is shown in FIG. 1 in that the illustrated instrument employs the forward-scattering principle of operation.

Light emitter 1 in conjunction with associated emitting optics 2 directs an emitted light beam 3 along the optical axis 4 of the emitted light. Here too the emitted light beam 3 extends through the optical end plate 5 into testing space 6. The continuation of the light beam strikes end plate 7 at the other end of testing space 6. After the emitted light beam 3 has traversed end plate 7, it reaches an optical shutter 8 that prevents an expansion of the emitted light beam while scattered light measurements are taken.

Contrary to the scattered light range of view measurement instrument shown in FIG. 1, the light receiver 10 and the associated receiving optics 11 shown in FIG. 2 are on the same side of testing space 6 as light emitter 1.

Emitted light beam 3 and received light beam 12 also cross each other inside testing space 6. This too generates a measurement zone 20 where particles $P^1$, $P^2$ to $P'''$ are illuminated by emitted light beam 3. In the back-scattering embodiment of FIG. 2, only that portion of the light which strikes particles $P^1$, $P^2$ to $P'''$ is deflected relative to the emitted light beam 4 by an angle $\beta$.

When using the back-scattering principle, the frequency with which particles in the measurement zone 20 are struck by light can be determined. From that, information can be derived about the range of sight through the gas sample in measurement zone 20.

As is true for the embodiment shown in FIG. 1, in the embodiment of FIG. 2 an obstacle in testing space 6 which interrupts the emitted light beam 3 in the area between end plate 5 and measurement zone 20 can lead to erroneous results.

To preclude such errors, the embodiment of FIG. 2 also includes an optical transmission path that can be activated with the help of the optical shutter 8.

In such an event, the portion of the emitted light beam received behind the boundary of testing space 6 is entrained in the received light beam 12 so that it too strikes light receiver 10.

In this manner, the embodiment of the invention illustrated in FIG. 2 also assures that the end plates which define the boundaries of the testing space are included in the transmission path and that the light transmissivity along all optical paths through the testing space 6 are monitored and controlled.

The electrical, optoelectronic and optical components of the instruments of the present invention are arranged outside the testing space 6, as is illustrated in FIGS. 1 and 2. Such components are preferably incorporated in an enclosed housing (not shown). The optical end plates 5, 7 and, if needed, additional ones are then integrated into the housing. It is also possible to install the components in two separate housings (not shown), which for example can be secured to each other with mechanical supports, connectors and the like. The needed light deflector can then be incorporated in the support or connector to protect it against possible mechanical damages.

What is claimed is:

1. Apparatus for determining a range of sight and capable of monitoring and correcting its operability comprising a light emitter for directing an emitted light beam to a measurement zone and a light receiver for receiving a received light beam from the measurement zone, the emitted light beam and the received light beam crossing each other in the measurement zone, a deflector for deflecting at least a portion of the emitted light beam downstream of the measurement zone along a light transmitting path and for directing the portion of the emitted light beam into the received light beam at a side of the measurement zone opposite from the light receiver, and an optical shutter for intermittently closing the light transmitting path in a temporally controlled manner.

2. Apparatus according to claim 1 wherein the optical shutter is positioned immediately in front of or behind the deflector.

3. Apparatus according to claim 1 wherein the optical shutter comprises a part of the deflector.

4. Apparatus according to claim 3 wherein the optical shutter is arranged inside the light deflector.

5. Apparatus according to claim 1 wherein the deflector comprises one of a flexible light conductor and a rigid light conductor.

6. Apparatus according to claim 5 wherein respective ends of the light conductor deflector include connectors for coupling and uncoupling the light conductor.

7. Apparatus according to claim 1 including an arrangement for cyclically opening and closing the optical shutter and therewith also the transmission light path through the deflector.

8. Apparatus according to claim 1 including a signal processor for determining an operability of the apparatus on the basis of values measured while the optical shutter is open.

9. Apparatus according to claim 8 wherein the signal processor includes a storage device in which values measured while the optical shutter was open are accumulated over a predeterminable period of time.

10. Apparatus according to claim 9 wherein the signal processor generates a signal when the accumulated measured values exceed a lower threshold value.

11. A method for determining a range of sight through a gas sample and for checking the accuracy of the determination, the method comprising providing a light emitter for emitting a light beam and a light receiver for receiving a light beam with a measuring zone arranged between the emitter and the receiver, directing the emitted light beam from the light emitter through the measurement zone so that the emitted and received beams cross each other in the measurement zone, generating scattered light in the measurement zone as a result of light from the emitted light beam striking particles present in the measurement zone, directing some of the scattered light as part of a received light beam to the light receiver, deflecting a portion of the emitted light beam after it has passed the measurement zone into a transmissions path and entraining the emitted light beam portion into the received light beam at a side of the measurement zone opposite the light receiver, and intermittently interrupting the deflecting step with an optical shutter to intermittently prevent entraining the emitted light beam portion into the received light beam.

12. A method according to claim 11 including providing a time responsive switching arrangement coupled to the optical shutter, and with the switching arrangement cyclically interrupting the deflecting step of the emitted light beam into the transmissions path.

13. A method according to claim 11 including providing a signal processing unit, and with the signal processing unit accumulating values measured while the optical shutter was open over a predetermined time interval.

14. A method according to claim 13 including generating a signal with the signal processing unit when the accumulated measured values drop below a threshold value.

15. A method according to claim 13 including generating a correction value for the scattered light measurements from the accumulated measured values.

* * * * *